United States Patent [19]

Barnett et al.

[11] Patent Number: 5,380,866

[45] Date of Patent: Jan. 10, 1995

[54] ALKYL SUBSTITUTED NITROIMIDAZOLE ACETIC ACIDS

[75] Inventors: Charles J. Barnett, Indianapolis; Thomas M. Wilson, Speedway, both of Ind.

[73] Assignee: Eli Lilly and Company, Indianapolis, Ind.

[21] Appl. No.: 214,889

[22] Filed: Mar. 15, 1994

Related U.S. Application Data

[62] Division of Ser. No. 49,915, Apr. 20, 1993.

[51] Int. Cl.$^6$ ............................................. C07D 233/64
[52] U.S. Cl. ................................ 548/330.1; 548/327.1
[58] Field of Search ........................... 548/330.1, 327.1

[56] References Cited

U.S. PATENT DOCUMENTS 4,925,949  5/1990  Massonneau et al. ............ 548/327.1
5,073,566  12/1991  Lifer et al. ............................ 514/381

OTHER PUBLICATIONS

Jacques, et al., *Enantiomers, Racemates, and Resolutions*, (John Wiley and Sons 1981).
CA 112 (19): 178783b Improved . . . nitroimidazoles. Searcey, et al., p. 750 (1990).
CA 115 (23): 256180f Preparation . . . antagonists. Lifer, et al., (1991).
CA 117 (3): 26418b Synthesis . . . arids. Suwinski, et al., p. 701 (1992).
Ca 117 (13): 131124a Nitroimidazoles . . . compounds. Suwinski, et al. (1992).

*Primary Examiner*—Mary C. Lee
*Assistant Examiner*—Joseph K. McKane
*Attorney, Agent, or Firm*—Steven P. Caltrider; David E. Boone

[57] ABSTRACT

This invention provides the substantially pure (R) enantiomer of a compound of the Formula II:

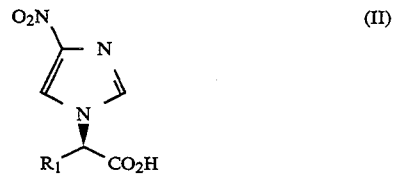

The compounds of Formula II are useful in the preparation of the substantially pure (R) enantiomer of angiotensin II antagonists of Formula III:

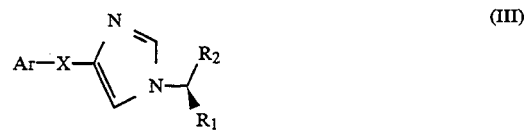

wherein $R_1$, Ar, $R_2$ and X are variables.

5 Claims, No Drawings

ALKYL SUBSTITUTED NITROIMIDAZOLE ACETIC ACIDS

This application is a division, of application Ser. No. 08/049,915, filed Apr. 20, 1993.

BACKGROUND OF THE INVENTION

The hormone angiotensin II is recognized as one of the most potent vasopressor agents that produces hypertension in mammals. The action of the enzyme renin on the plasma protein substrate angiotensinogen results in production of the inactive decapeptide angiotensin I, which upon conversion by the nonselective angiotensin converting enzyme (ACE) provides angiotensin II the active hormone. See e.g. Regoli et al., *Pharm. Rev.* 26:69 (1974).

U.S. Pat. No. 5,073,566 and U.S. patent application Ser. No. 07/892,867 disclose potent and effective 1,3-imidazoles, as angiotensin II antagonists of the Formula I:

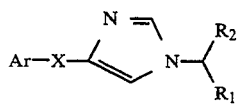
(I)

These compounds may exist in various stereoisomeric forms. In particular, the compounds exist as enantiomers due to the chiral carbon atom to which the imidazole, $R_1$, and $R_2$ are attached. U.S. Pat. No. 5,073,566 and U.S. patent application Ser. No. 892,867 disclose the separation of the enantiomers by chromatographic separation of an intermediate or the final product. The obvious shortcomings of chromatographic separation are inefficiency and expense. The separation is particularly inefficient if the separation is performed as the final step where one-half of the final product may be discarded as the undesired enantiomer.

The present invention provides compounds that are useful as intermediates in the preparation of the substantially pure (R) enantiomer of angiotensin antagonists of Formula I.

The compounds of the present invention are prepared by a process generally characterized as an optical resolution. See Jacques, et al., *Enantiomers, Racemates, and Resolutions* (John Wiley and Sons 1981). Unfortunately, when attempting to apply these general teachings to efficiently separate enantiomers, it is impossible to determine what conditions or resolving agents will be successful. In the present invention, resolving agents such as brucine, ephedrine, quinidine, cinchonine, and quinine produced unacceptable mixtures of diastereoisomeric salts. Thus, the present invention further provides a process of preparing the compounds of the present invention by disclosing a remarkably effective resolving agent that selectively crystallizes the substantially pure enantiomer.

SUMMARY OF THE INVENTION

This invention provides the substantially pure (R) enantiomer of a compound of the Formula II:

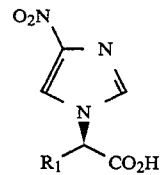
(II)

wherein $R_1$ is $C_4$–$C_9$ straight chain alkyl, $C_4$–$C_9$ straight chain trifluoroalkyl, $C_4$–$C_9$ straight chain alkenyl, or $C_4$–$C_9$ straight chain trifluoroalkenyl.

In addition, this invention provides the (−)-cinchonidine salt of compounds of the Formula II.

The invention further provides a method of preparing the compounds of Formula II, comprising:

(a) reacting a racemic mixture of the compound of the Formula IV

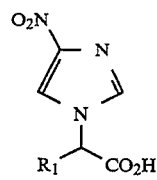
(IV)

wherein $R_1$ is $C_4$–$C_9$ straight chain alkyl, $C_4$–$C_9$ straight chain trifluoroalkyl, $C_4$–$C_9$ straight chain alkenyl, or $C_4$–$C_9$ straight chain trifluoroalkenyl; with (−)-cinchonidine in an alcoholic solvent in the presence or absence of a $C_1$-$C_4$ alkyl amine to produce a crystalline salt;

(b) isolating the crystalline salt;

(c) optionally converting the crystalline salt to the free acid thereby producing a substantially pure (R) enantiomer of the Formula II:

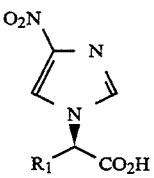
(II)

wherein $R_1$ is $C_4$–$C_9$ straight chain alkyl, $C_4$–$C_9$ straight chain trifluoroalkyl, $C_4$–$C_9$ straight chain alkenyl, or $C_4$–$C_9$ straight chain trifluoroalkenyl.

The compounds of Formula II are useful in the preparation of the substantially pure (R) enantiomer of angiotensin II antagonists of Formula III:

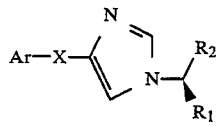
(III)

wherein:

Ar is phenyl substituted with $R_9$ and $R_{11}$;

X is —CONH—;

$R_1$ is $C_4$–$C_9$ straight chain alkyl, $C_4$–$C_9$ straight chain trifluoroalkyl, $C_4$–$C_9$ straight chain alkenyl, or $C_4$–$C_9$ straight chain trifluoroalkenyl;

$R_2$ is —CONH ($C_1$–$C_4$ alkyl), —CONH (hydroxy-$C_1$–$C_4$ alkyl), —CONH($C_1$–$C_4$ trifluoroalkyl), (a) 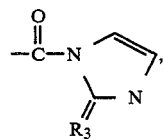

(b) 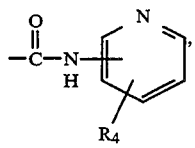

(c) 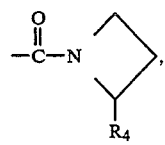

(d) 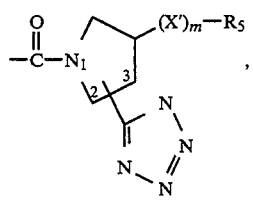

(e) 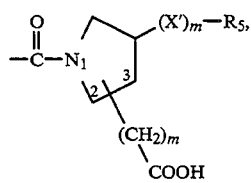

(f) 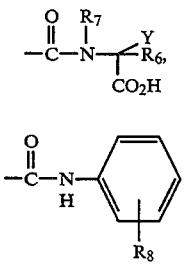

(g) 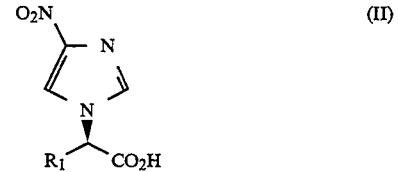

$R_4$ is $(CH_2)_pR_9$, or $C_1$-$C_4$ alkyl;

$R_5$ is H, —$(CH_2)_pR_9$, $C_1$-$C_7$ alkyl, $C_1$-$C_7$ trifluoroalkyl, halo, substituted or unsubstituted phenyl, 3-pyridyl, 2-pyrimidyl, furanyl, oxazolyl, isoxazolyl, a substituted or unsubstituted fused bicyclic, a substituted or unsubstituted fused tricyclic, or when m is 0, 4,4-ethylenedioxy;

$R_6$ is H or —$(CH_2)_qR_{10}$;

$R_7$ is H or $CH_3$;

$R_8$ is H, OH, $C_1$-$C_4$ alkoxy, $CO_2H$, $SO_3H$, $PO_3H_2$, $CONHSO_2R_5$, or tetrazolyl;

$R_9$ is $CO_2H$, $SO_3H$, $PO_3H_2$, $CONHSO_2R_5$ or 5-tetrazolyl;

$R_{10}$ is OH, $NH_2$, or $CO_2H$;

$R_{11}$ is H, —OH, —$OCOCH_3$, halo, $C_1$-$C_4$ alkyl, amino, acetamido, or $C_1$-$C_4$ alkoxy;

Y is a R group of a naturally occurring amino acid;

X' is —O—, —$(CH_2)_p$—, or —S—;

m is independently 0 or 1;

p is independently 0, 1, 2, 3 or 4;

q is independently 1, 2, 3, or 4;

providing that when $R_2$ is (d) or (e) and $R_5$ is not H, the carboxy of (e) or tetrazolyl of (d is in position 2; and when $R_2$ is (d) or (e), m is 0, and $R_5$ is H, the carboxy of (e) or tetrazolyl of (d) is in position 2 or 3.

DETAILED DESCRIPTION AND PREFERRED EMBODIMENT

As noted above, the invention provides compounds of the Formula II that are useful as intermediates of 1,3-imidazole angiotensin II antagonists.

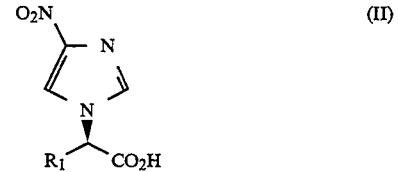

U.S. Pat. No. 5,073,566 and U.S. patent application Ser. No. 07/892,867 disclose 1,3 imidazole angiotensin II antagonists and derivatives thereof. U.S. Pat. No. 5,073,566 is herein incorporated by reference.

The terms "$C_1$-$C_4$ alkyl," "$C_1$-$C_7$ alkyl," and "$C_1$-$C_9$ alkyl" represent a cyclo, straight or branched chain alkyl group having from one to four, seven or nine carbon atoms respectively such as methyl, ethyl, n-propyl, isopropyl, n-butyl, isobutyl, sec-butyl, t-butyl, cyclopropylmethyl, pentyl, isopentyl, cyclopentyl, 1-methylbutyl, 1-ethylpropyl, neopentyl, tert-pentyl, n-hexyl, isohexyl, 4-methyl hexyl, cyclohexyl, cyclohexylmethyl, n-heptyl, t-heptyl, iso-heptyl and the like.

The term "hydroxy-$C_1$-$C_4$ alkyl" is a $C_1$-$C_4$ alkyl substituted with a hydroxy. A hydroxy-$C_1$-$C_4$ alkyl is preferably of the formula $HO(CH_2)_q$—, where q is 1 to 4.

The terms "$C_1$-$C_4$ trifluoroalkyl" and "$C_1$-$C_7$ trifluoroalkyl" represent a straight or branched chain alkyl group having from one to four or seven carbon atoms respectively in which the primary carbon is substituted with fluorine.

The term "$C_4$-$C_9$ straight chain alkyl" represents a straight chain alkyl group having from four to nine carbon atoms. Examples of a "$C_4$-$C_9$ straight chain alkyl" include n-butyl, n-pentyl, n-hexyl, n-heptyl, n-octyl, and n-nonyl.

The term "$C_4$-$C_9$ straight chain trifluoroalkyl" represents a $C_4$-$C_9$ straight chain trifluoroalkyl group in which the primary carbon is substituted with fluorine.

The terms "$C_1$-$C_4$ alkoxy" and "$C_1$-$C_7$ alkoxy" represent $C_1$-$C_4$ or $C_1$-$C_7$ alkyl group covalently bonded to the parent moiety by an —O— linkage.

The terms "$C_1$-$C_4$ trifluoroalkoxy" and "$C_1$-$C_7$ trifluoroalkoxy" represent $C_1$-$C_4$ or $C_1$-$C_7$ trifluoroalkyl group covalently bonded to the parent moiety by an linkage.

The term "$C_4$-$C_9$ straight chain alkenyl" represents a straight chain alkenyl group having from four to nine carbon atoms and one double bond. Examples of a "$C_4$-$C_9$ straight chain alkenyl" include n-butenyl, pentenyl, n-hexenyl, n-heptenyl, n-octenyl, and n-nonenyl.

The term "$C_4$-$C_9$ straight chain trifluoroalkenyl" represents a $C_4$-$C_9$ straight chain alkenyl group in which the primary carbon atom is trisubstituted with fluorine. Examples of a "$C_4$-$C_9$ straight chain trifluoroalkenyl" include 4-trifluoro-n-2-butenyl, 5-trifluoro-n-2-pentenyl, 6-trifluoro-n-3-hexenyl, 7-trifluoro-n-4-heptenyl, 8-trifluoro-n-6-octenyl, and 9-trifluoro-n-5-nonenyl.

The term "R group of a naturally occurring amino acid" represents the variable region of the naturally occurring amino acids and is understood in the art. See, for example, Lehninger A. L. Biochemistry, 2nd edition. Worth Publishers, p. 73–75 1975.

The term "—$(CH_2)_pR_9$" represents a straight chain alkyl, branched alkyl, or a straight chain alkenyl bonded to $R_9$ or $R_9$ when p is zero. Examples of "—$(CH_2)_pR_9$" include groups in which the straight chain alkyl, branched alkyl or straight chain alkenyl portion includes methylene, ethylene, trimethylene, tetramethylene, methylethylene, ethylethylene, 2-methyltrimethylene, ethenylene, propenylene, and butenylene.

The term "halo" includes fluoro, chloro, bromo, and iodo.

The term "substituted or unsubstituted phenyl" represents phenyl or phenyl substituted with one or two groups independently selected from —$(CH_2)_pR_9$, —$(CH_2)_pR_9$, —$(CF_2)_pCO_2H$, $C_1$-$C_7$ alkyl, $C_1$-$C_7$ trifluoroalkyl, halo, —$(CH_2)_pOH$, cyano, phenylsulfenyl, phenyl, thiophenyl, thiocarboxy, $C_1$-$C_7$ trifluoroalkoxy, $C_1$-$C_7$ alkoxy, —$S(C_1$-$C_4$ alkyl), —$SO(C_1$-$C_9$ alkyl), —$SO_2(C_1$-$C_9$ alkyl), —$SO_2NR_{14}R_{15}$, —$(CH_2)_pCONR_{14}R_{15}$, —$(CH_2)_pNR_{16}SO_2$ ($C_1$-$C_4$ alkyl or $C_1$-$C_4$ trifluoroalkyl), or a heteroaryl selected from imidazolyl, triazolyl, tetrazolyl, thioazolyl, isoxazolyl or oxazolyl, said heteroaryl being optionally substituted with —$(CH_2)_pR_9$; $R_{14}$ and $R_{15}$ are independently H, $C_1$-$C_4$ alkyl, —$(CH_2)_pCOOH$ or taken together with nitrogen to which they are bonded constitute a heterocylic ring selected from the groups consisting of pyrrolidino or piperidino, said heterocylic ring being optionally substituted with —COOH; $R_{16}$ is H or $C_1$-$C_4$ alkyl. Preferably, a substituted or unsubstituted phenyl is a phenyl substituted with one substituent, preferably —$(CH_2)R_9$.

The term "fused bicyclic" represents a stable fused bicyclic ring system of the formula:

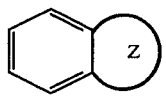

wherein Z represents a substituted or unsubstituted, saturated or unsaturated 5 or 6 membered ring, said ring having from zero to three heteroatoms that are the same or different and that are selected from the group consisting of sulfur, oxygen, and nitrogen; and when z contains two adjacent carbon atoms, the adjacent carbon atoms may be structured to form a group of the formula —CH=CH—CH=CH—; provided that (1) when the heterocyclic ring contains 5 members, the heteroatoms comprise not more than one sulfur or two oxygen atoms but not both; (2) when the heterocyclic ring contains 6 members, sulfur and oxygen are not present; and (3) when the heterocyclic ring contains a sulfur or oxygen atom, the benzofusion is joined to a carbon adjacent to said sulfur or oxygen atom. The fused bicyclic may be attached at any carbon which affords a stable structure. The fused bicyclic may be substituted with one or two groups independently selected from —$(CH_2)_pR_9$, —$O(CH_2)_pR_9$, —$(CF_2)_pCO_2H$, $C_1$-$C_7$ alkyl, $C_1$-$C_7$ trifluoroalkyl, halo, —$(CH_2)_pOH$, cyano, phenylsulfenyl, phenyl, thiophenyl, thiocarboxy, $C_1$-$C_7$ trifluoroalkoxy, $C_1$-$C_7$ alkoxy, —$S(C_1$-$C_4$ alkyl), —$SO(C_1$-$C_9$ alkyl), —$SO_2(C_1$-$C_9$ alkyl), —$SO_2NR_{14}R_{15}$, —$(CH_2)_pCONR_{14}R_{15}$, —$(CH_2)_pNR_{16}SO_2$ ($C_1$-$C_4$ alkyl or trifluoroalkyl), or a heteroaryl selected from imidazolyl, triazolyl, tetrazolyl, thioazolyl, isoxazolyl or oxazolyl, said heteroaryl being optionally substituted with —$(CH_2)_pR_9$; $R_{14}$ and $R_{15}$ are independently H, $C_1$-$C_4$ alkyl, —$(CH_2)_pCOOH$ or taken together with nitrogen to which they are bonded constitute a heterocylic ring selected from the groups consisting of pyrrolidino or piperidino, said heterocylic ring being optionally substituted with —COOH; $R_{16}$ is H or $C_1$-$C_4$ alkyl.

The term "fused tricyclic" represents a stable fused tricyclic ring system of the formula:

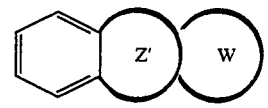

wherein Z' represents a saturated or unsaturated 5 membered ring, said ring having zero or one heteroatom that is selected from the group consisting of sulfur, oxygen, and nitrogen; W represents a substituted or unsubstituted, saturated or unsaturated 6 membered ring, said ring having from zero to three nitrogen atoms. The fused tricyclic may be attached at any carbon which affords a stable structure. The fused tricyclic may be substituted with one or two groups independently selected from —$(CH_2)_pR_9$, —$O(CH_2)_pR_9$, —$(CF_2)_pCO_2H$, $C_1$-$C_7$ alkyl, $C_1$-$C_7$ trifluoroalkyl, halo, —$(CH_2)_pOH$, cyano, phenylsulfenyl, phenyl, thiophenyl, thiocarboxy, $C_1$-$C_7$ trifluoroalkoxy, $C_1$-$C_7$ alkoxy, —$S(C_1$-$C_4$ alkyl), —$SO(C_1$-$C_9$ alkyl), —$SO_2(C_1$-$C_9$ alkyl), —$SO_2NR_{14}R_{15}$, —$(CH_2)_pCONR_{14}R_{15}$, —$(CH_2)_pNR_{16}SO_2$) $C_1$-$C_4$ alkyl or trifluoroalkyl), or a heteroaryl selected from imidazolyl, triazolyl, tetrazolyl, thioazolyl, isoxazolyl or oxazolyl, said heteroaryl being optionally substituted with —$(CH_2)_pR_9$; $R_{14}$ and $R_{15}$ are independently H, $C_{1-4}$ alkyl, —$(CH_2)_pCOOH$ or taken together with nitrogen to which they are bonded constitute a heterocylic ring selected from the groups consisting of pyrrolidino or piperidino, said heterocylic ring being optionally substituted with —COOH; $R_{16}$ is H or $C_1$-$C_4$ alkyl.

Ar is phenyl substituted with $R_9$ and $R_{11}$ wherein $R_{11}$ is H, —OH, —$OCOCH_3$, halo, $C_1$-$C_4$ alkyl, amino, acetamido, or $C_1$-$C_4$ alkoxy. Ar is preferably substituted with a single substituent. Host preferably $R_9$ is $SO_3H$, and $R_{11}$ is H.

The term "carboxy protecting group" as used in the specification refers to one of the ester derivatives of the carboxylic acid group commonly employed to block or protect the carboxylic acid group while reactions are carried out on other functional groups on the compound. The species of carboxy-protecting group employed is not critical so long as the derivatized carboxylic acid is stable to the condition of subsequent reaction(s) and can be removed at the appropriate point without disrupting the remainder of the molecule. See E. Haslam, *Protective Groups in Organic Chemistry*, J. G. W. McOmie, Ed., Plenum Press, New York, N.Y., 1973, Chapter 5, and T. W. Greene, *Protective Groups in Organic Synthesis*, John Wiley and Sons, New York, N.Y., 1981, Chapter 5. A related term is "protected carboxy," which refers to a carboxy-protecting groups.

The term "amino protecting group" as used in the specification refers to substituents of the amino group commonly employed to block or protect the amino functionality while reacting other functional groups on the compound. The species of amino protecting group employed is not critical so long as the derivatized amino group is stable to the condition of subsequent reaction(s) and can be removed at the appropriate point without disrupting the remainder of the molecule. Preferred amino protecting groups are t-butoxycarbonyl and the benzyloxycarbonyl. See J. W. Barton, *Protective Groups in Organic Chemistry*, J. G. W. McOmie, Ed., Plenum Press, New York, N.Y., 1973, Chapter 2, and T. W. Greene, *Protective Groups in Organic Synthesis*, John Wiley and Sons, New York, N.Y., 1981, Chapter 7. The related term "protected amino" defines an amino group substituted with an amino protecting group as previously discussed.

The term "$C_1$–$C_4$ alkyl amine" represents a $(R_{20})_3N$ wherein $R_{20}$ is independently H or $C_1$–$C_4$ alkyl.

Formula IV represents a racemic mixture of the enantiomers of the Formula II and V.

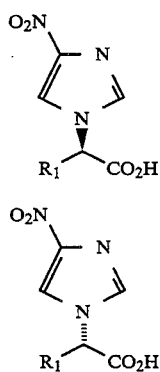

The compounds of Formula IV may be prepared by methods known in the art. For example, 4-nitroimidazole can be converted to its sodium salt by reaction with either sodium hydride or sodium hydroxide in DMF solution, and subsequently alkylated with a suitable α-bromo acid ester. Conventional hydrolysis of the product gives rise to compounds of Formula IV. Typically, sodium hydride is washed, if necessary, with a hydrocarbon solvent to remove residual mineral oil and suspended in dry DMP. A suspension of 4-nitroimidazole in DMF is added and the mixture stirred until hydrogen evolution ceases. The desired alkylating agent, for example ethyl 2-bromooctanoate, is added and the mixture stirred until complete conversion of starting material has been obtained. The reaction mixture is then diluted with water and extracted with ethyl acetate. The resulting ethyl acetate solution is dried and concentrated to obtain the desired (4-nitroimidazol-1-yl)ester which may be hydrolyzed to the corresponding acid by conventional methods.

The resolution of the compounds of Formula IV into the desired enantiomer, Formula II, is accomplished using (−)-cinchonidine as the resolving agent. When (−)-cinchonidine is reacted with a solution containing the compounds of Formula IV, a crystalline salt of the (R) enantiomer forms. This salt may be separated from the reaction mixture by known techniques such as filtration. The other enantiomer, Formula V, remains in the filtrate. The crystalline salt of the desired enantiomer can be further purified by recrystallization.

Therefore, the compounds of the Formula II may be prepared by a process comprising:

(a) reacting a racemic mixture of the compound of the Formula IV

wherein $R_1$ is $C_4$–$C_9$ straight chain alkyl, $C_4$–$C_9$ straight chain trifluoroalkyl, $C_4$–$C_9$ straight chain alkenyl, or $C_9$ straight chain trifluoroalkenyl; with of (−)-cinchonidine in an alcoholic solvent in the presence or absence of a $C_1$–$C_4$ alkyl amine to produce a crystalline salt;

(b) isolating the crystalline salt;

(c) optionally converting the crystalline salt to the free acid thereby producing a substantially pure (R) enantiomer of the Formula II:

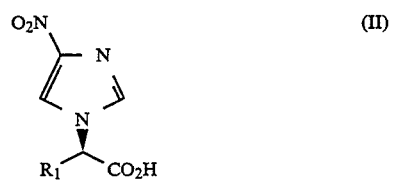

wherein $R_1$ is $C_4$–$C_9$ straight chain alkyl, $C_4$–$C_9$ straight chain trifluoroalkyl, $C_4$–$C_9$ straight chain alkenyl, or $C_4$–$C_9$ straight chain trifluoroalkenyl.

An alcoholic solvent includes ethanol, ethanol and water, methanol, methanol and water, a mixture of methanol and ethanol in water, and the like. The preferred alcoholic solvent is ethanol and water.

Due to the expense of (−)-cinchonidine, it is preferred that a portion of the (−)-cinchonidine is replaced with a $C_1$–$C_4$ alkyl amine, preferably triethylamine. Therefore, the preferred resolution is carried out with one-half equivalent of the (−)-cinchonidine and one-half equivalent a $C_1$–$C_4$ alkyl amine. When a $C_1$–$C_4$ alkyl amine is added to the process, the ratio of ethanol to water may vary from about 100:0 to 1:3, with the optimum ratio of about 1:2. The solvent volume (defining the solvent volume for the crystallization as mL solvent mixture/g of racemic acid) with the addition of triethylamine is preferably about 5 mL/g to 12 mL/g.

The reaction preferably occurs at a pH of about 6.9–7.4. The crystalline salt may be isolated by standard methods known in the art. Preferably, the salt is isolated by filtration.

Preferred compounds of this invention are those compounds of Formula II wherein $R_1$ is $C_4$–$C_9$ straight chain alkyl. A particularly preferred compound is the cinchonidine salt. The (−)-cinchonidine salt selectively crystallizes from a racemic mixture of 2-alkyl substituted-4-nitro-imidazole acetic acids of the Formula IV to yield the (R) enantiomer (−)-cinchonidine salt in greater than 90% stereoisomeric purity. Further, by recrystallizing the (−)-cinchonidine salt from an aqueous alcohol, greater than 98% stereoisomeric purity may be obtained.

Recrystallization comprises dissolving the resulting salt in a second solvent comprising an alcoholic solvent, and crystallizing the compound from the second solvent to provide a recrystallized salt. The recrystallization is preferably carried out in ethanol and water. The ratio of solvent to water is not critical to the invention and may vary from about 100:0 to 1:1, with the optimum ratio of about 1:1. The solvent volume (defining the solvent volume for the recrystallization as mL solvent mixture/g of salt) likewise is not critical to operability of the invention but preferably is between 4 mL/g to 40 mL/g.

A number of other optically active resolving agents were tried as potential resolving agents. Other agents include brucine, ephedrine, quinidine, cinchonine, and quinine. These agents failed to separate the enantiomers, instead producing or unacceptable mixtures of diastereoisomeric salts. Thus, (−)-cinchonidine appears to be a remarkably effective resolving agent that produces a salt that selectively crystallizes the desired, substantially pure enantiomer.

As previously stated, the compounds of Formula II are useful as intermediates to prepare the substantially pure R enantiomer of 1,3-imidazoles disclosed in U.S. Pat. No. 5,073,066 and U.S. patent application Ser No. 892,867. The compounds of the Formula II are therefore useful to prepare angiotensin II antagonist of the Formula III.

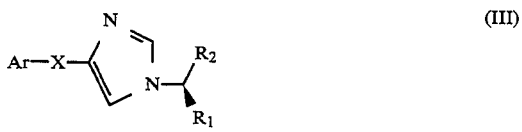

(III)

wherein Ar, X, $R_1$, and $R_2$ are the same as previously defined.

The compounds of the Formula III are prepared by coupling a compound of Formula II to a compound of the formula

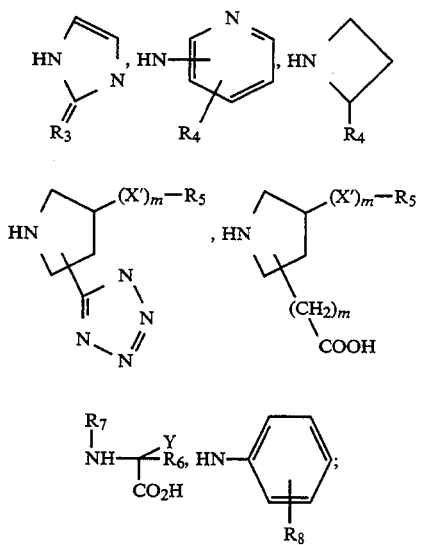

wherein $R_3$, $R_4$, $R_5$, $R_6$, $R_7$ and $R_8$ are the same as previously defined;

reducing the nitro of Formula II to produce an amino imidazole;

and coupling the amino imidazole to a compound of the formula:

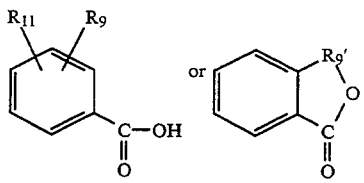

wherein $R_9$ and $R_{11}$ are the same as previously defined; $R_9'$ is $SO_2$ or $C=O$.

The coupling of carboxylic acid to an amine may be accomplished by any of several known methods For example, the carboxylic acid moiety may be transformed into its corresponding acid halide, preferably the acid chloride. The conversion of an carboxylic acid to an acid halide is readily accomplished by techniques known in the art. For example, the conversion may be accomplished upon treatment with a reagent such as thionyl chloride or oxalyl chloride optionally in the presence of an aprotic nonreactive solvent. The acid halide may then be coupled to the amine by any of several known methods. The preferred method in this invention is to react the acid halide with the amine directly in THF or methylene chloride in the presence of triethylamine.

Alternatively, other amide condensing reagents may also be employed, such as 1,1'-carbonyldiimidazole or 1,3-dicyclohexylcarbodiimide. These reagents are usually employed in a nonreactive high boiling solvent such as dimethylformamide and optionally in the presence of reagents such as diisopropylethylamine, hydroxybenzotriazole, and the like in order to facilitate reaction.

If $R_2$ contains a carboxy moiety (for example, when $R_2$ is (e)), the reaction is best carried out as a protected carboxy. Preferably, the carboxy is protected as an ester. When the coupling is complete, the ester may be readily converted into the acid by methods known in the art. For example, the ester moiety may be hydrolyzed with an aqueous base such as 2N NaOH in methanol. The pH lowered to 3.0 with 5N HCL. The acid product may then be extracted by conventional means.

One skilled in the art would appreciate that the reactants, in particular the amines, the substituted benzoic acids, or the substituted anhydride, are commercially available, known in the art, or can be prepared by methods known in the art.

The coupling of the substituted benzoic acid or the substituted anhydride to the imidazole may occur at any time in the synthesis. Preferably, the compound of Formula II is converted into an acid halide, reacted with the amine, reduced and then coupled to the substituted benzoic acid or the substituted anhydride to produce the 1,3-imidazole angiotensin II antagonist. However, one skilled in the art would appreciate that the order of the reactions is not critical as long as appropriate amino and carboxy protecting groups are employed.

When preparing compounds wherein $R_9$ is $CO_2H$ or $SO_3H$, it is preferred that the anhydride, for example a sulfobenzoic cyclic anhydride, be employed in the preparation of compounds of the Formula III. The anhydride is reacted by mixing the two reagents in one or more nonreactive solvents, such as dimethylformamide.

The compounds of the Formula II are particularly useful in preparing the compounds of Formula IIIa:

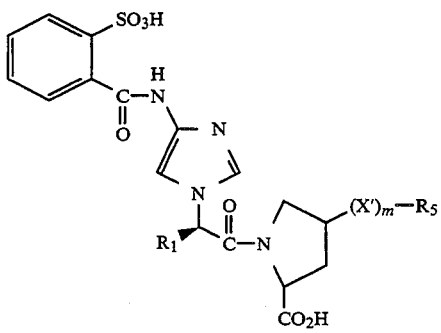

(IIIa)

wherein $R_1$ is a $C_4$-$C_9$ straight chain alkyl; $R_5$ is an unsubstituted or para substituted phenyl, a substituted or unsubstituted fused bicyclic, or substituted or unsubstituted fused tricyclic; m is 0 or 1; X' is —O—, —S—, or $(CH_2)_p$; and p is 0, 1, 2, 3 or 4.

The most preferred compounds that may be prepared are those compounds in which X' is —O—, and $R_5$ is a substituted phenyl of the formula:

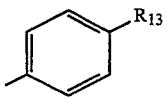

wherein $R_{13}$ is —$(CH_2)_pR_9$, —$O(CH_2)_pR_9$, —$SO_2NR_{14}R_{15}$, $(CH_2)_pCONR_{14}R_{15}$, —$(CH_2)_pNR_{16}SO_2$ ($C_1$-$C_4$ alkyl or $C_1$-$C_4$ trifluoroalkyl) or a heteroaryl selected from imidazolyl, triazolyl, tetrazolyl, thiozolyl, isoxazolyl, or oxazolyl, said heteroaryl being optionally substituted with —$(CH_2)_pR_9$; $R_{14}$ and $R_{15}$ are independently H, $C_{1-4}$ alkyl, —$(CH_2)_pCOOH$ or taken together with nitrogen to which they are bonded constitute a heterocylic ring selected from the groups consisting of pyrrolidino or piperidino, said heterocyclic ring being optionally substituted with —COOH; $R_{16}$ is H or $C_1$-$C_4$ alkyl. Preferred compounds are compounds of the Formula III wherein $R_{13}$ is —$(CH_2)_pR_9$; and $R_9$ is $CO_2H$ or $PO_3H_2$; and p is 1.

The following examples and preparations are provided merely to further illustrate the invention. The scope of the invention is not construed as merely consisting of the following examples.

In the following examples and preparations, melting point, nuclear magnetic resonance spectra, mass spectra, high pressure liquid chromatography ever silica gel, N,N-dimethylformamide, palladium on charcoal, enantiomeric excess, and tetrahydrofuran are abbreviated M.Pt., NMR, MS, HPLC, DMF, Pd/C, ee, and THF, respectively. The terms "NMR" and "MS" indicate that the spectrum was consistent with the desired structure.

Preparation 1

N-Carbobenzyloxy-4-trans-hydroxy-L-proline methyl ester

A solution of silver oxide (I) (1.08 moles, 250 g) in 1500 ml acetone was cooled to −5°-0° C. N-carbobenzyloxy-4-trans-hydroxy-L-proline (0.5 moles, 132.6 g) was added. The solution was stirred for 25 minutes. Methyl iodide (1.2 moles, 170.4 g) was added at −6° C. over 25 minutes. The reaction was stirred at room temperature for 5 hours, filtered, and concentrated. The intermediate was dissolved in ethyl acetate, filtered through silica gel and concentrated. (MS)

Calculated for $C_{14}H_{17}NO_5$: C, 60.21; H, 6.13; N, 5.01. Found: C, 60.40; H, 6.26; N, 5.06.

Preparation 2

N-Carbobenzyloxy-4-cis-phenoxy-L-proline methyl ester

N-Carbobenzyloxy-4-trans-hydroxy-L-proline methyl ester (0.267 moles, 74.5 g), phenol (0.282 moles, 26.5 g), and triphenylphosphine (0.279 moles, 73.3 g) were dissolved in 750 ml of THF, and cooled to −3° C. Diethyl azidodicarboxylate (0.284 moles, 45 ml) was added dropwise over 2 hours. The reaction was stirred at room temperature overnight and then concentrated. The residue was dissolved in ether, filtered and concentrated. The intermediate was chromatographed over silica gel eluted with a gradient of 0–40% ethyl acetate in hexane to yield 41.0 g. (NMR)

Preparation 3

4-cis-phenoxy-L-proline methyl ester

N-Carbobenzyloxy-4-trans-hydroxy-L-proline methyl ester (0.267 moles, 74.5 g), phenol (0.282 moles, 26.5 g), and triphenylphosphine (0.279 moles, 73.3 g) were dissolved in 750 ml of THF, and cooled to −3° C. Diethyl azidodicarboxylate ( 0.284 moles, 45 ml) was added dropwise over 2 hours. The reaction was stirred at room temperature overnight and then concentrated. The residue was dissolved in ether, filtered and concentrated. The intermediate was chromatographed over silica gel eluted with a gradient of 0–40% ethyl acetate in hexane. The protecting group was removed. (NMR)

EXAMPLE 1

(R)-α-hexyl-4-nitro-1H-imidazole-1-acetic acid cinchonidine salt

To a suspension of 5.89 g (0.02 mol) of (−)-cinchonidine in 80 mL water was added 2.78 mL (2.02 g, 0.02 mol) triethylamine. The mixture was warmed to about 40°-45° C. A solution of 10.21 g (0.04 mol) of a racemic mixture of α-hexyl-4-nitro-1H-imidazole-1-acetic acid in 40 mL technical grade ethanol was added to the warm suspension with stirring. (The pH of the mixture was adjusted to 6.9–7.4 by addition of triethylamine or aqueous hydrochloric acid as required.) The resulting suspension was then heated to about 85° C. The resulting solution was allowed to cool gradually to ambient temperature with slow stirring. The precipitated salt was filtered, washed with about 30 mL of ethanol —$H_2O$ (1:2), and dried at 50° C. in vacuo to constant weight. The reaction produced 9 g of (R)-α-hexyl-4-nitro-1H-imidazole-1-acetic acid (−)-cinchonidine salt. A portion of the product was converted to the free acid and then derivatized as the methyl ester (diazomethane) and analyzed by HPLC on a chiral column. The analysis indicated that the acid derived from the product had an ee of 94%. Recrystallization of the produce salt from ethanol-water 1:1 (13:1 volumes) provided 7.4 g of the pure salt, ee>99% (HPLC), M.Pt. 205° C. (dec). (NMR).

Calculated for $C_{30}H_{39}N_5O_5$: C: 65.55; H, 7.15; N, 12.74.

Found: C: 65.32; H, 7.25; N, 12.74.

EXAMPLE 2

(R)-α-hexyl-4-nitro-1H-imidazole-1-acetic acid

A 2.80 g portion of the pure cinchonidine salt obtained as described in Example 1 was mixed with 20 mL of 1M HCL. The resulting suspension was extracted with 30 mL of ethyl acetate. The ethyl acetate phase was dried (MgSO4) and concentrated to dryness, providing 0.82 g (63%) of (R)-α-hexyl-4-nitro-1H-imidazole-1-acetic acid. M.Pt. 112°–114° C.

EXAMPLE 3

Cis-4-[4-(carboxymethyl)phenoxy]-1-(1-oxo-2(R)-[4-nitro-1H-imidazole-1-yl ]octyl-L-proline Combined (R) -α-hexyl-4-nitro-1H-imidazole-1-acetic acid (100 mg, 0.39 mmol) with 4-cis-(4-carboxymethylphenoxy)-L-proline methyl ester (120 mg, 0.39 mmol ) and THF. Hydroxybenzotriazole ( 57 mg, 0.42 mmol ) was added at 0° C. Dicyclohexylcarbodiimide (88 mg, 0.42 ) was added, and the solution stirred for 30 minutes. The solution was warmed to room temperature. The resulting precipitate was removed by filtration, and the filtrate was concentrated to produce a oil. The oil was diluted with 5 ml of ethyl acetate, washed with 3 ml of saturated NaHCO3, 3 ml of 1M HCl, 3 ml of saturated NaHCO3, dried with MgSO4 and concentrated to yield 145 mg of cis-4-[4-(carboxymethyl)-phenoxy]-1-(1-oxo-2(R)-[4-nitro-1H-imidazole-1-yl]octyl-L-proline. (NMR).

EXAMPLE 4

Cis-4-[4-(carboxymethyl)phenoxy]-1-[1-oxo-2-sulfobenzoyl)amino]-1H- imidazo-1-yl]octyl]-L-proline Cis-4-[4-(carboxymethyl)phenoxy]-1-(1-oxo-2(R)-[4-nitro-1H-imidazol-1-yl]octyl-L-proline methyl ester is reduced by hydrogenation at 40 psi over Pd/C. The reaction is filtered and concentrated. The residue is dissolved in THF and added to 2-sulfobenzoic cyclic anhydride in THF. The product is isolated by filtration and is dried in vacuo to yield cis-4-[4-(carboxymethyl)-phenoxy]-1-[1-oxo-2(R)-[4-[(2-sulfobenzoyl)amino]-1H-imidazol-1-yl]octyl]-L-proline methyl ester. The ester is hydrolyzed to yield the title product.

EXAMPLE 5

(R)-1-[1-oxo-2-[4-(2-sulfobenzoyl)amino-1H-imidazol-1-yl]octyl]-4-(cis)-[(4-(methylene-N-methanesulfonamido))-phenoxy]-L-proline To a solution of N-carbobenzyloxy-trans-4-hydroxy-L-proline methyl ester (10.0 g, 35.8 mmol) in 200 mL of anhydrous THF under N2 was added triphenylphosphine (10.6 g, 39.4 mmol) and 4-cyanophenol (4.7 g, 39.4 mmol). This solution was cooled to 0° C. and then treated with diethylazodicarboxylate (6.3 mL, 39.4 mmol), added dropwise over 30 minutes. The reaction was warmed to room temperature and stirred for 2 days. The solvent was removed in vacuo, and the residue chromatographed (SiO2, 30% ethyl acetate/hexanes) to provide 12.1 g (89%) of N-carbobenzyloxy-4-(cis)-(4-cyanophenoxy)-L-proline methyl ester as a colorless oil. (MS).

Calculated for $C_{21}H_{20}N_2O_5$: C, 66.31; H, 5.30; N, 7.36.

Found: C, 66.10; H, 5.34; N, 7.50.

To a solution of N-carbobenzyloxy-4-(cis)-(4-cyanophenoxy)-L-proline methyl ester (3.8 g, 10 mmol) in 75 mL of methanol was added COCl2 (2.6 g, 20 mmol).

This solution was cooled to 0° C. and then treated with NaBH4 (3.8 g, 100 mmol), added in small portions. After stirring for 2 hours, 50 mL of 3N HCl were added. After stirring this solution for 15 minutes, the reaction was distributed between H2O/ether (200 mL ea.). The layers were separated, and the aqueous was extracted with ether (2×100 mL). The aqueous phase was then made basic with concentrated NH4OH solution. Extraction with ethyl acetate (3×100 mL), followed by drying (Na2SO4) and concentration in vacuo provided 3.50 g (90%) of N-carbobenzyloxy-4-(cis)-[(4-aminomethyl)-phenoxy]-L-proline methyl ester as an oil. This material was used in the next reaction without further purification. (MS).

Calculated for $C_{21}H_{24}N_2O_5$: C, 65.61; H, 6.29; N, 7.29.

Found: C, 65.87; H, 6.04; N, 7.03.

To a solution of N-carbobenzyloxy-4-(cis)-[(4-aminomethyl)-phenoxy]-L-proline methyl ester (0.90 g, 2.34 mmol) in 15 mL of anhydrous CH2Cl2 was added N,N-diisopropylamine (0.6 mL, 3.4 mmol). This solution was cooled to 0° C. and then treated with methanesulfonylchloride (0.22 mL, 2.8 mmol), added as a solution in 5 mL of CH2Cl2. After stirring for 1.5 h, the reaction was distributed between ethyl acetate/H2O (50 mL ea.). The layers were separated, and the aqueous was extracted with ethyl acetate (2×50 mL). The organic was dried (Na2SO4) and concentrated in vacuo to give a crude oil. Chromatography (SiO2, 50/50 ethyl acetate/hexanes) provided 0.74 g (70%) of N-carbobenzyloxy-4-(cis)-[(4—(methylene-N-methanesulfonamido))-phenoxy]-L-proline methyl ester as a colorless oil. (MS).

To a solution of (−)-cinchonidine (48.0 g, 163 mmol) in 880 mL of distilled H2O at room temperature was added 2-(4-nitro-1H-imidazol-1-yl)-octanoic acid 83.0 g, 326 mmol) as a solution in 440 mL of ethanol. To this mixture was added triethylamine (11.7 mL). The mixture was then heated to 80° C., and the pH was maintained between 6.9 and 7.1 by the dropwise addition of triethylamine (5–10 mL). After the pH stabilized at 7.01, the solution was allowed to cool to room temperature, and let stand overnight whereupon crystallization of the (R)-2—(4-nitro-1H-imidazol-1-yl)-octanoic acid-cinchonidine salt occurred. The crystalline salt was collected by filtration. The salt was then suspended 200 mL ea. of ethyl acetate/H2O. To this suspension was added in HCl (750 mL). The layers were separated, and the aqueous was extracted with ethyl acetate (2×500 mL). The organic was combined, dried (Na2SO4), and concentrated in vacuo to provide 29.9 g (72%) of (R)-2-(4-nitro-1H-imidazol-1-yl)-octanoic acid as an off-white solid. M.Pt. 116°–118° C.

Calculated for $C_{11}H_{17}N_3O_4$: C, 51.76; H, 6.71; N, 16.46.

Found: C, 51.89; H, 6.76; N, 16.20.

Enantiomeric excess was determined to be 96% by conversion of the acid to its methyl ester (diazomethane), followed by HPLC analysis employing a chiral column.

(R)-2-(4-nitro-1H-imidazol-1-yl)-octanoic acid (16.0 g, 63.0 mmol) was dissolved in 1 L of anhydrous methanol. To this solution was added pTsOH (300 mg). The reaction was then heated to reflux for 16 hours. Upon cooling, the solvent was removed in vacuo, to give an oil that was dissolved in 300 mL of ethyl acetate. The solution was washed (2×250 mL) with saturated NaH- CO₃ solution The organic was then dried (Na₂SO₄) and concentrated in vacuo to provide 13.2 g (78%) of (R)-methyl-2-(4-nitro-1H-imidazol-1-yl)-octanoate as an amber oil.

Calculated for C₁₂H₁₉N₃O₄: C, 53.32; H, 7.11; N, 15.6.

Found: C, 53.23; H, 7.05; N, 15.39.

(R)-Methyl-2-(4-Nitro-1H-imidazol-1-yl)octanoate (13.0 g, 45.7 mmol) was dissolved in 150 mL of absolute ethanol. To this solution was added 2.0 g of 10% Pd/C. The mixture was hydrogenated at 40 psi for 2 hours. The catalyst was then removed by passing the reaction through a bed of celite. The filtrate was then concentrated to an oil that was evaporated twice from anhydrous THF (100 mL). The crude product was then dissolved in 100 mL of anhydrous THF and treated with KOAc (4.44 g) and K₂CO₃ (3.12 g). To this mixture was added sulfobenzoic anhydride (8.83 g, 47.7 mmol). The reaction was stirred for 4 hours after which time a precipitate formed. The mixture was diluted with THF (100 mL) and the solid collected by filtration. Drying in vacuo provided 22.5 g of crude (R)-methyl-[(2-sulfobenzoyl)amino-1H-imidazol-1-yl]-octanoate-potassium salt. This material was carried on to the next reaction without further purification.

The potassium salt (22.5 g) was dissolved in a mixture of 200 mL H₂O and 100 mL of ethanol. To this solution was added 1N NaOH (53 mL). The reaction was allowed to stir for 3 hours. The solvent ethanol was then removed in vacuo, and the aqueous acidified to pH=1.5 with 5N HCl. This solution was extracted with 10% ethanol/ethyl acetate (3×200 mL). The organic was dried (Na₂SO₄) and concentrated in vacuo to give 8.65 g (46% for two steps) of (R)-[(2-sulfobenzoyl)amino-1H-imidazol-1-yl]-octanoic acid as a white solid. MS.

Calculated for C₁₈H₂₃N₃O₆S: C, 52.80; H, 5.66; N, 10.26.

Found: C, 52.53; H, 5.59; N, 10.27.

To a solution of N-carbobenzyloxy-4-(cis)-[(4-(methylene-N-methanesulfonamido))-phenoxy]-L-proline methyl ester (1.5 g, 3.25 mmol) in 50 mL of absolute ethanol was added 0.5 g of 5% Pd/C. This mixture was hydrogenated at 40 psi for 1.5 hours. The reaction mixture was then passed through a pad of celite, and the filtrate concentrated in vacuo to give 1.07 g of 4-(cis)-[(4-(methylene-N-methanesulfonamido))-phenoxy]-L-proline methyl ester as an oil. MS. This material was used immediately in the next reaction.

To a solution of the above amine in 10 mL of anhydrous DMF was added (R)-[(2-sulfobenzoyl)amino-1H-imidazol-1-yl]-octanoic acid (1.00 g, 2.45 mmol) and hydroxybenzotriazole (0.37 g, 2.77 mmol). This mixture was cooled to 0° C., and then treated with dicyclohexylcarbodiimide (0.56 g, 2.70 mmol). The resulting solution was warmed to room temperature and stirred for 48 hours. After removal of dicyclohexylurea by filtration, the filtrate was diluted with 100 mL of ethyl acetate and washed several times with H₂O. The organic was then dried (Na₂SO₄) and concentrated in vacuo to an oil. Chromatography (SiO₂, 5% methanol/CHCl₃) provided 0.84 g (34%) of (R)-1-[1-oxo-2-[4-(2-sulfobenzoyl)amino-1H-imidazol-1-yl]octyl]-4-(cis)-[(4-(methylene-N-methanesulfonamido))-phenoxy]-L-proline methyl ester as a white solid. M.Pt. 150° C. (dec).

Calculated for C₃₂H₄₁N₅O₁₀S₂: C, 53.40; H, 5.74; N, 9.73.

Found: C, 53.66; H, 5.97; N, 9.50.

R)-1-[1-oxo-2-[4-(2-sulfobenzoyl)amino-1H-imidazol-1-yl]octyl]-4-(cis)-[(4-(methylene-N-methanesulfonamido))-phenoxy]-L-proline methyl ester<0.37 g, 0.52 mmol) was dissolved in a mixture of 1N NaOH (3.0 mL) and THF (7 mL). This solution was stirred for t hour. The THF was then removed in vacuo, and the aqueous was acidified to pH 1.0 using 1N HCl. Extraction with 5% ethanol/ethyl acetate (2×) followed by drying (Na₂SO₄) of the organic and concentration yielded a solid residue. Trituration from ethanol/ethyl acetate-ether provided 0.26 g (74%) of (R)-1-[1-oxo-2-[4-(2-sulfobenzoyl)amino-1H-imidazol-1-yl]octyl]-4-(cis)-[(4-(methylene-N-methanesulfonamido))-phenoxy]-L-proline as an off-white solid. M.Pt. 172°–176° C.

Calculated for C₃₁H₃₉N₅O₁₀S₂: C, 52.75; H, 5.57; N, 9.92.

Found: C, 52.54; H, 5.53; N, 10.15.

We claim:

1. A compound of the Formula (II)

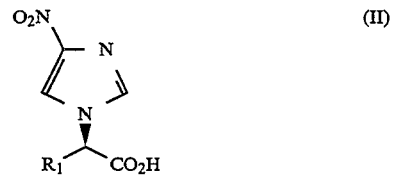

wherein the configuration is substantially the (R) enantiomer, and R₁ is C₄–C₉ straight chain alkyl, C₄–C₉ straight chain trifluoroalkyl, C₄–C₉ straight chain alkenyl, or C₄–C₉ straight chain trifluoroalkenyl; or a (−)-cinchonidine salt thereof.

2. The salt of (−)-cinchonidine and a compound to the Formula II:

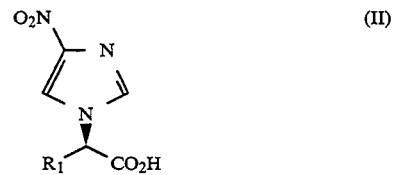

wherein the configuration is substantially the (R) enantiomer, and R₁ is C₄–C₉ straight chain alkyl, C₄–C₉ straight chain trifluoroalkyl, C₄–C₉ straight chain alkenyl, or C₄–C₉ straight chain trifluoroalkenyl.

3. A compound of the Formula (II)

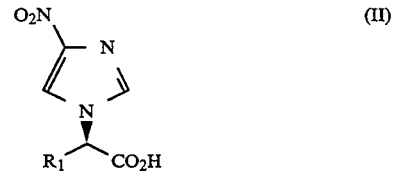

wherein the configuration is substantially the enantiomer, and R₁ is C₄–C₉ straight chain alkyl, C₄–C₉ straight chain trifluoroalkyl, C₄–C₉ straight chain alkenyl, or C₄–C₉ straight chain trifluoroalkenyl.

4. A compound of claim 3 which is substantially (R)-α-hexyl-4-nitro-1H-imidazole-1-acetic acid.

5. A compound of claim 2 which is substantially (R)-αhexyl-4-nitro-1H-imidazole-1-acetic acid (−-cinchonidine salt.

* * * * *

UNITED STATES PATENT AND TRADEMARK OFFICE
CERTIFICATE OF CORRECTION

PATENT NO. : 5,380,866
DATED : January 10, 1995
INVENTOR(S) : Charles J. Barnett, et al.

It is certified that error appears in the above-indentified patent and that said Letters Patent is hereby corrected as shown below:

Column 16, line 58 - after the word "the", insert the letter -- (R) --.
Column 16, line 65 - after the phrase "(-", insert -- ) --.

Signed and Sealed this

Ninth Day of May, 1995

Attest:

BRUCE LEHMAN

Attesting Officer

Commissioner of Patents and Trademarks